United States Patent [19]

Bar-On

[11] 4,003,989

[45] Jan. 18, 1977

[54] PHARMACEUTICAL PREPARATION

[76] Inventor: Ernest Bar-On, 3 Pasternak St., Tel-Aviv, Israel

[22] Filed: Apr. 24, 1975

[21] Appl. No.: 571,430

[30] Foreign Application Priority Data

May 6, 1974 Israel .................... 44774

[52] U.S. Cl. ................... 424/43; 424/230; 424/301
[51] Int. Cl.[2] ............ A61K 9/00; A61K 31/60; A61K 31/265
[58] Field of Search ............ 424/230–234, 424/43, 44, 301

[56] References Cited

UNITED STATES PATENTS

| | | | |
|---|---|---|---|
| 2,211,485 | 8/1940 | Zimmermann | 424/44 |
| 3,136,692 | 6/1964 | Bondelin | 424/44 |
| 3,608,064 | 9/1971 | Lamb | 424/230 |

*Primary Examiner*—Stanley J. Friedman
*Attorney, Agent, or Firm*—Weingarten, Maxham & Schurgin

[57] ABSTRACT

A pharmaceutical preparation, for oral ingestion after dissolution in a suitable palatable liquid, comprising in combination acetylsalicylic acid, a solubilizing agent adapted to result in a substantially complete dissolution of the acetylsalicylic acid and dry milk solids in a quantity of from 10 to 100 times the weight of the active ingredient. The preferred solubilizing agent is a combination of physiologically acceptable alkali metal carbonate and bicarbonate. The preparations are preferably provided in unit dosage form in the form of a fine powdery mixture sealed in a moisture-proof package.

12 Claims, No Drawings

PHARMACEUTICAL PREPARATION

BACKGROUND OF THE INVENTION

The present invention relates to a novel pharmaceutically active composition of matter comprising as active ingredient acetylsalicylic acid or sodium salicylate. More particularly, the present invention relates to a novel pharmaceutically active, water-soluble composition of matter comprising acetyl salicylic acid or sodium salicylate as active ingredient, said composition being adapted to substantially reduce, or entirely eliminate undesired side-effects encountered with acetylsalicylic acid and with sodium salicylate. The novel composition of matter are readily soluble in water and comprise ingredients adapted to result in a rapid and complete solubilization of the active ingredient, and in a buffering action, the combined effect being the substantial reduction or elimination of undesired side-effects. The novel pharmaceutical compositions are soluble in water, and results in a palatable pleasant drink, very much similar to natural milk, and this is easily administered to children and to other persons like the aged, physically and mentally retarded and the like, who experience difficulties in swallowing pills. Any desired suitable flavouring agent may be added.

The invention further relates to such novel compositions of matter in unit dosage form. Other and further aspects of the present invention will become apparent hereinafter.

Acetylsalicylic acid is probably the most widely used analgesic, antipyretic and antirheumatic compound. Acetylsalicylic acid is considered to be the best painkiller amongst common drugs, as reported by an investigating team of the Mayo Clinic, U.S.A. (reported in April 1972). Although used in huge quantities, acetylsalicylic acid is known to cause undesired side effects, and especially gastrointestinal disturbances, in a certain percentage of patients. The first evidence that acetylsalicylic acid is not so innocuous as it appeared to be came from English physicians in the late 1930's (Brit.Med.J. (1938), 1143; Lancet (1938), 12222; Lancet (1954) 917; Brit.Med.J. (1943) 768; Brit.-Med.J. (1958), 1062; Brit.Med.J. (1955), 1531; Lancet (1958) 920, etc. A large quantity of information on this subject matter is summarized in "Aspirin and Gastric Damage", A. Muir, Scientific Exhibit, A.M.A. Convention, Atlantic City, N.J. June 8–12, 1959. Amongst the most common side effects there may be mentioned gastro-duodenal bleeding, dyspepsia, and erosive gastritis. From the results it can be concluded that aspirin is a potentially dangerous drug, especially in ulcer patients, but also in some eupeptic individuals. Bleeding is commoner in elderly people who have taken the drug in heavy dosage over a considerable period of time. The drug is a potent actual or precipitating cause of gastro-duodenal bleeding. Batterman (New Eng.J.Med. 1958, 258, 213,) deals in detail with the relative merits of aspirin and buffered aspirin (aspirin 300 mg. dihydroxy-aluminum amino-acetate 100 mg., magnesium carbonate 100 mg.) and comes to the conclusion that times required for analgesia and the degree of analgesia were identical. Also, the frequency of gastro-intestinal intolerance were identical for both buffered and unbuffered aspirin. In U.S. Pat. No. 3,608,064 (Lamb) there is described milk-buffered aspirin. Aspirin is used in powdered or granular form and the ratio of aspirin to milk solids exemplified is about 1:1 by weight. No solubilization is resorted to Comparative results with such compositions of matter are presented in the last Table of this specification. Hereinafter results are presented showing the advantages of the novel composition of matter according to the invention compared with aspirin, with buffered aspirin and with aspirin in combination with milk solids only. Many of the buffered aspirins have the added drawback of gradual decomposition, the decomposition products being still less tolerable than acetylsalicylic acid by itself.

The conventional pharmaceutical compositions containing acetylsalicylic acid or sodium salicylate as active ingredient are generally supplied in unit dosage form in the form of tablets. A certain percentage of patients experience difficulties in the swallowing of such tablets. Amongst these are certain physically or mentally retarded persons, such a those suffering from cerebral palsy, CNS-impairment, hydrocephaly, hemiplegia, Downs syndrome and the like. Some of the conventional preparations in tablet form, integrate completely upon swallowing and cause severe local effects on the mucosa of the stomach.

Quite frequently infants and children ingest large quantities of aspirin tablets and severe effects, including a multitude of cases of death, are caused thereby. Statistics on the fatality rate of such ingestion in the United States are quite surprising and show a large number of fatalities per year.

SUMMARY OF THE INVENTION

The present invention relates to a pharmaceutical preparation, for oral ingestion, after dissolution in a suitable liquid, comprising in combination acetylsalicylic acid, a solubilizing agent adapted to result in the substantially complete dissolution of the acetylsalicylic acid, and dry milk solids in a quantity of from 10 to 100 times by weight with respect to the active ingredient.

The above drawbacks are eliminated or at least substantially decreased by the novel compositions of matter according to the present invention. The novel pharmaceutically active compositions of matter according to the present invention comprise in combination acetylsalicylic acid with a solubilizing agent and with a substantial quantity of dry milk solids or sodium salicylate with a substantial quantity of dry milk solids. The said solubilizing agent is used in a quantity adapted to bring about the complete solubilization of the active ingredient. The dry milk solids are advantageously used in a quantity of about 5 to 100 times the weight of the active salicylic acid or salicylate. A preferred ratio is from 10 to 100 times. The solubilizing agent is used in conjunction with acetylsalicylic acid; when water-soluble sodium salycilate is used, no solubilizing agent need be used, and this compound is used in conjunction with dry milk solids in a similar weight ratio. The compositions are preferably supplied in unit dosage form.

According to preferred embodiment of the invention, a sweetening agent is added, and if desired, also a flavouring agent. When the novel compositions of matter are dissolved in water, a pleasant tasting drink, very similar to natural milk in taste, is obtained. They can also be dissolved in milk.

The solubilizing agent of choice comprises in combination a physiologically acceptable alkali metal or alkaline earth metal carbonate and bicarbonate in a predetermined ratio. Preferred are sodium bicarbonate and potassium bicarbonate and preferred carbonates are sodium carbonate, potassium carbonate or calcium carbonate. The mixture of bicarbonate and carbonate is used in a quantity to ensure the complete solubilization of the acetylsalicylic acid. Advantageously about a molar ratio and up to an excess of about 10 to 15 per cent with respect to the molar ratio is used. Results have shown that for the solubilization of 100 g. acetylsalicylic acid a mixture of about 57 g. potassium bicarbonate and about 6.6 g. potassium carbonate gives best results. Similar results can be obtained with about 63 g. sodium bicarbonate and 6.6 g. sodium carbonate. Similar results are obtained when these quantities are varied by about 5 per cent downwards, and up to by about 10 per cent above these quantities. It is clear that mixtures of such sodium and potassium salts may be used. It is stressed that the novel pharmaceutical compositions can be stored in the dry state over prolonged periods of time (for some years), without any perceptible deterioration. This is contrary to accepted belief that mixtures of acetylsalicylic acid and sodium bicarbonate cannot be stored as they tend to become gummy (see Merck Index). The carbonate brings about a stabilization of the composition. A suitable ratio of carbonate to bicarbonate is from about 1 to 8 and up to 1 to 25 by weight.

The dry milk solids can be of any conventional composition, but they ought to be as dry as possible. It is advantageous to take commercially available dry milk solids, preferably of the type containing little fat, and to subject these to a further drying step, so as to obtain as dry a product as conveniently possible. Preferably the humidity ought not to exceed about 1% by weight, and the lower the humidity, the better are the storage properties of the product. Dry milk solids of the non-fat type are preferred. Spray-dried solids are preferred due to the rapid dissolution of same. Freeze-dried solids give good results. It is clear that these ought to be of the type used for humans. The moisture content of commercial milk solids is up to about 3.6 per cent by weight. Such products are advantageously further dried, preferably under reduced pressure. A number of samples of commercially available dry milk solids were tested and it was found that these had a moisture content of from about 2.0 to 3.5 per cent by weight. Best results were obtained with non-fat dry milk solids of up to about 1.0 per cent moisture content. Slightly inferior results were obtained with whole-milk powder with a moisture content of about the same.

There can be added any desired sweetening or flavouring agents which are compatible with the above ingredients. It is advantageous to add a sweetener such as saccharine, possibly with a flavouring agent like cocoa powder, vanilla or the like.

The actate ingredient acetylsalicylic acid or sodium salicylate, is used in dry and finely powdered form, advantageously of 20 to 200 mesh, U.S. standard sieve size, and this is mixed with the other ingredients, which too ought to be dry and in finely powdered form of similar mesh size. The intimately mixed compositions are advantageously filled in a suitable dry environment in unit dosage quantities into individual packages of water-impervious material, such as metal-foil lined paper or plastic. Such hermetically sealed unit dosage form preparations can be stored over prolonged periods of time without deterioration. Some samples were prepared and stored for a period of over 4 years. No perceptible change or deterioration of the ingredients took place during this time. The content of a unit dosage package is dissolved prior to ingestion in a predetermined quantity of water, it dissolves quickly and the thus obtained liquid is taken orally. It can also be dissolved in milk. Tests have shown that the active ingredients are effectively absorbed from the gastrointestinal tract. Gastrointestinal disturbances are substantially less than with conventional tablets of acetylsalicylic acid or with conventional preparations of buffered aspirin. This is evident from tests carried out. Conventional dosages of the active ingredient can be administered as required.

The following examples are intended to illustrate the present invention and these are to be construed in a nonlimitative manner.

EXAMPLE 1

An intimate mixture was prepared, consisting of:

Example 1:
An intimate mixture was prepared, consisting of:
| | |
|---|---|
| Acetylsalicylic acid, dry, 40–100 mesh | 60 g. |
| Potassium bicarbonate, dry, fine powder | 35 g. |
| Potassium carbonate, dry, fine powder | 4.2 g. |

The powdery substances were thoroughly mixed in a dry atmosphere.

The thus obtained mixture (100 g.) was added gradually under stirring to a quantity of 4.4 kg. of non-fat dry milk powder, dried to a moister content of 0.8 per cent by weight. The ingredients were stirred until a homogenous mixture was attained.

Quantities of 22.5 g. each were prepared and sealed in hermetically closed packages of polyethylene-lined aluminum foil. Each of the resulting packages contained 0.3 g. acetylsalicylic acid.

The packages were stored during 12 months at 30° C. in an external atmosphere of high humidity. No deterioration of the content took place during this period.

The content of a package of 22.5 g. was dissolved in 100 ml. of tap water. It dissolved rapidly giving a drink resembling natural milk in taste and this was drunk. The beneficial results of the active ingredient were obtained with no gastric disturbances.

EXAMPLE 2

The active substance was prepared as above, but with the addition of 1.5 g. sodium salt of saccharine. After admixture with the milk solids, there were prepared packages of 37.5 g. of the mixture and these were sealed. Each of these contained 0.5 g. of aspirin. No deterioration took place during 2 years. A dosage unit was dissolved in a glass of water and could be easily drunk.

EXAMPLE 3

Further batches were prepared, but instead of the non-fat milk powder there was used spray-dried, whole-milk powder. This had a moisture content of 0.55 per cent by weight. It contained 26% fat and 26.3% proteins. Similar quantities were used and the results were practically identical.

EXAMPLE 4

A soluble mixture was prepared from:

Example 4:
A soluble mixture was prepared from:
| | |
|---|---|
| Acetylsalicylic acid, 20–100 mesh | 57 g. |

| | |
|---|---|
| -continued | |
| Sodium carbonate | 3.8 g. |
| Sodium bicarbonate | 37 g. |
| Saccharine | 1.2 g. |

The powdered substances were thoroughly mixed and to the thus obtained 100 g. of active soluble mixture there were added 3.2 kg. of non-fat dry milk solids and the mixture was thoroughly mixed in a dry atmosphere.

From the resulting powder there were prepared unit doses of 17 g. each containing about 0.3 g. of acetylsalicylic acid. These were hermetically sealed. Prolonged storage (3 years) did not result in a deterioration or decomposition of the active ingredient. The content of each package was dissolved in half a glass of water and drunk.

The experiments reported herein were carried out by the Head of the Department of Gastroenterology, Hadassa Hebrew University Medical Center, Jerusalem.

Absorption of the above compositions of matter from the gastro-intestinal tract was determined in animals and by human volunteers.

In the animal experiments rats were used and each of these was given a quantity of 100 mg. acetylsalicylic acid in a mixture according to Example 1, dissolved in drinking water. Urinary salicylate levels were determined after 2, 4 and 6 hours respectively after ingestion; blood levels were determined after 15 minutes. Average blood levels of 34.5 mg% were found with acetylsalicylic acid and of 31 mg. with the above composition.

Urinary excretion of salicylate shows that the compositions according to the present invention are excreted slightly more quickly than acetylsalicylic acid alone.

The acetylsalicylic acid used for comparison was a well known commercial brand.

In human volunteers it was found that 6 hours after drug administration the excretion of salicylate amounts to 30.4% of the total quantity ingested with compositions according to the invention, compared with 27% of acetylsalicylic acid ingested by itself.

The above results show that the compositions according to the present invention are absorbed more rapidly and that these are also excreted more rapidly. The compositions according to the invention showed no undesired side effects.

In view of the undesired side effects of acetylsalicylic acid as such, and of certain buffered compositions, it was decided to compare the effects of well known brands of these, which are known to be of good quality and of comparatively minor side effects as compared with other lesser known brands, with compositions of the present invention.

The materials tested were Aspirin (Bayer), (ASA), and Alka Seltzer (AZ), compared with compositions according to the present invention (according to examples 1 and 4), designated AM.

Fasted male rats were used in these studies. Pyloric ligation was performed under light ether anaesthesia and the following solutions were administered intragastrically;

10 mg/100 g. Bayer Aspirin (8 rats) (ASA)
10 mg/100 g. Alka Seltzer (8 rats) (AZ)
10 mg/100 g. AM (14 rats)
1 ml/100 g. 0.9% NaCl (25 rats)

Four hours after this, gastrectomy was performed following ligation of the oesophagus. Gastric juice from the stomach was emptied through a funnel into calibrated centrifuge tubes. The stomach was examined for the presence of gastric bleeding. Acid concentration was measured by titration with 0.05 N NaOH using Toepfer's reagent and phenolphthalein as indicators. Aspirin concentration was determined in the gastric juice and sodium salicylate concentrations were determined in the blood plasma at the end of the experimental period.

ASA and AM decrease significantly gastric secretion, compared with control rats which received saline only. Total acid output was significantly decreased following ASA only. The following values of the effects of intragastric administration of ASA, AZ and AM, 10mg/100 g. of animal weight on gastric secretion in pyloric ligated rats were obtained:

| | Volume ml/4 hrs. | Free Acid mEq/4 hrs | Total Acid mEq/4 hrs. |
|---|---|---|---|
| ASA | | | |
| No. of Exper. | 7 | 7 | 7 |
| Average± S D | 6.6±0.74 | 0.68±0.09 | 0.80±0.13 |
| AZ | | | |
| No. of Exper. | 8 | 8 | 8 |
| Average± S D | 7.6±2.2 | 0.58±0.40 | 1.01±0.41 |
| AM | | | |
| No. of Exper. | 14 | 14 | 14 |
| Average± S D | 6.5±1.47 | 0.53±0.23 | 0.95±0.26 |

Blood concentration of sodium salicylate 4 hours after intragastric administration of ASA, AZ and AM, 10 mg/100 g. was as follows:

| | ASA | AZ | AM |
|---|---|---|---|
| No. of Experiments | 8 | 8 | 12 |
| Na-salicylate, mg Average ± S D | 16.9±3.5 | 16.7±3.4 | 14.1±1.7 |
| Test T | | | |
| ASA-AM | $t=2.26, p\ 0.05$ | | |
| AZ - AM | $t=2.14, p=0.05$ | | |

Results obtained with rats with pyloric ligated stomachs show that there exists no significant difference between ASA, AZ and AM as regards the degree of absorption of acetylsalicylic acid from the stomach.

Most significant and important results were obtained as to erosions, which signify the damaging effect on the mucosa of the stomach. In the control group of 25 rats, which received saline only, only 2 out of the 25 rats were found to have erosions. In the group of 8 rats which received ASA, all the rats were found to have bleedings and erosions, averaging 2.75 erosions per rat. In the AZ group of 8 rats, 7 out of 8 rats were found to have erosions, averaging 2.87 per rat. In the AM group of 14 rats, 8 out of the 14 had erosions, averaging 0.86 erosions per rat. This proves that AM in contact with mucosa during 4 hours in pyloric ligated rats has the lowest damaging effect on the mucosa, the values given above being statistically highly significant.

TABLE

Effects of Intragastric Administration of acetyl salicylic acid (ASA), Alka-Selzer (AZ), Aspirmilk, (acc. to present invention (AM), aspirin with milk (1:1 by weight, solids) (A+M) on gastric secretion and on the mucosa in pyloric ligated rats

|  | CONTROL | ASA 10mg/100g | AZ 10mg/100g | AM 10mg/100g | A+M 10mg/100g |
|---|---|---|---|---|---|
| Volume in ml/4h/100 g |  |  |  |  |  |
| n | 15 | 12 | 13 | 19 | 7 |
| average±2SD | 4.05±0.50 | 4.50±0.26 | 5.80±1.00 | 4.20±0.60 | 4.50±1.14 |
| Total acid mEq/4h/100g |  |  |  |  |  |
| n | 15 | 12 | 13 | 19 | 7 |
| average±2SD | 0.46±0.06 | 0.53±0.05 | 0.74±0.12 | 0.61±0.08 | 0.44±0.16/ |
| Gastric pepsinogen, mg/4h/100 g |  |  |  |  |  |
| n | 15 | 5 | 5 | 5 | 7 |
| average±2SD | 6.88±0.98 | 3.98±0.88 | 9.09±1.00 | 6.07±1.78 | 5.41±1.60 |
| Gastric salicylate cont. mg/4h |  |  |  |  |  |
| n | 7 | 7 | 8 | 12 | 7 |
| average±2SD |  | 0.53±0.14 | 1.91±0.76 | 1.23±0.38 | 0.43±0.10 |
| Erosions/rat |  | 1.7 | 1.5 | 0.8 | 2.1 |
| Bleedings/rat(>2mm) |  | 1.9 | 1.75 | 0.6 | 2.4 |
| Bleedings/rat(<2mm) |  | 3.5 | 1.75 | 1.0 | 1.0 |
| Perforation |  |  |  |  | one rat |
| Erosions+bleedings/rat | 1.06 | 7.1 | 5.0 | 2.4 | 5.6 |

The above Table summarizes the effect of aspirin combined with an equal weight of dry milk solids (according to U.S. Pat. No. 3,608,064) on changes in the mucosa in pyloric ligated rats. Pyloric ligation was performed in eight fasted male rats under light ether anaesthesia and 10mg/100 g of aspirin with milk (1:1) were administered intragastrically. Four hours later gastrectomy was performed. The stomach was examined for the presence of erosions and bleedings, larger or smaller than 2 mm. Acid and salicylate concentrations and peptic activity were measured in the gastric juice obtained from the pyloric ligated stomach. In one of the rats no gastric juice was found due to perforation. Results are compared with results obtained with ASA, AZ and AM under similar conditions.

From the above it is clear that the novel compositions of matter cause significantly less gastric disturbance and damage. The novel compositions of matter are easily administered to infants, children and the infirm or ill, as it is obtained after dissolution in the form of a palatable drink nearly identical in its taste with natural milk. The novel preparations have excellent storage properties, and the danger of accidental ingestion of large numbers of tablets by infants and children is prevented.

Unit dosage preparations were prepared comprising about 0.3 to 0.6 g. sodium salicylate in combination with about 6 to 30 g. of dry milk solids, and these were packed in humidity-proof packages. Storage during 24 months did not bring about a deterioration of these compositions of matter. Upon dissolution in about 100 ml. of water, a palatable drink, similar in taste to natural milk was obtained. The active ingredient exerted its usual effects upon oral ingestion. Undesired side effects were substantially decreased.

It is clear that the above description is by way of illustration only and that modifications and changes in the details of the composition and preparation can be resorted to without departing from the scope and spirit of the present invention.

What is claimed is:

1. A pharmaceutical preparation in unit dosage form for oral ingestion after dissolution in a suitable liquid, said pharmaceutical preparation comprising in combination sodium salicylate and a quantity of 5 to 100 times by weight thereof of dry milk solids.

2. A pharmaceutical preparation according to claim 1, packaged in a moisture-proof, unit-dosage package.

3. A pharmaceutical preparation for oral ingestion after dissolution in a suitable liquid, said pharmaceutical preparation comprising in combination:
   acetylsalicylic acid;
   a combined solubilizing agent selected in part from the group consisting of potassium bicarbonate and sodium bicarbonate and selected in part from the group consisting of potassium carbonate and sodium carbonate, said combined solubilizing agent being of sufficient quantity to result in substantially complete dissolution of said acetylsalicylic acid; and
   dry milk solids in a quantity ranging from 5 times to 100 times by weight of said acetylsalicylic acid.

4. The pharmaceutical preparation according to claim 3 wherein the weight ratio of the bicarbonate element to the carbonate element in said combined solubilizing agent ranges from 8:1 to 25:1.

5. The pharmaceutical preparation according to claim 3 wherein said bicarbonate is used in a quantity ranging from 5 per cent less than the molar ratio with respect to said acetylsalicylic acid to 50 per cent greater than the molar ratio with respect to said acetylsalicylic acid.

6. The pharmaceutical preparation according to claim 3 wherein said acetylsalicylic acid and said combined solubilizing agent are of small particle size, the composition having a moisture content of less than 1 per cent by weight calculated on the total weight of the composition.

7. The pharmaceutical preparation according to claim 3 wherein said acetylsalicylic acid, said combined solubilizing agent and said dry milk solids are in powdered form.

8. The pharmaceutical preparation according to claim 7 in unit dosage form comprising a hermetically sealed moisture-proof package enclosing the powdered dry ingredients.

9. The pharmaceutical preparation according to claim 3 and further comprising a sweetening agent.

10. The pharmaceutical preparation according to claim 3 and further comprising a flavouring agent.

11. The pharmaceutical preparation according to claim 1 and further comprising a sweetening agent.

12. The pharmaceutical preparation according to claim 1 and further comprising a flavouring agent.

* * * * *